(12) United States Patent
Nussaume et al.

(10) Patent No.: US 9,801,373 B2
(45) Date of Patent: Oct. 31, 2017

(54) COMPOUNDS FOR ALLEVIATING PHOSPHATE STARVATION SYMPTOMS IN PLANTS

(71) Applicant: Commissariat a l'Energie Atomique et aux Energies Alternatives, Paris (FR)

(72) Inventors: Laurent Nussaume, La Tour d'Aigues (FR); Carole Arnaud, Saint-Quentin-la-Chabanne (FR); Mathilde Clement, Vallauris (FR); Thierry Desnos, Pertuis (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 6 days.

(21) Appl. No.: 14/438,498

(22) PCT Filed: Oct. 25, 2013

(86) PCT No.: PCT/EP2013/072429
§ 371 (c)(1),
(2) Date: Apr. 24, 2015

(87) PCT Pub. No.: WO2014/064265
PCT Pub. Date: May 1, 2014

(65) Prior Publication Data
US 2015/0272119 A1    Oct. 1, 2015

(30) Foreign Application Priority Data

Oct. 25, 2012 (EP) .................................... 12190024

(51) Int. Cl.
| | | |
|---|---|---|
| A01N 31/08 | (2006.01) |
| A01N 41/12 | (2006.01) |
| A01N 41/10 | (2006.01) |
| A01N 31/16 | (2006.01) |
| C05G 3/00 | (2006.01) |
| G01N 33/50 | (2006.01) |

(52) U.S. Cl.
CPC ............. *A01N 41/12* (2013.01); *A01N 31/08* (2013.01); *A01N 31/16* (2013.01); *A01N 41/10* (2013.01); *C05G 3/00* (2013.01); *G01N 33/5097* (2013.01)

(58) Field of Classification Search
None
See application file for complete search history.

(56) References Cited

U.S. PATENT DOCUMENTS

| | | | |
|---|---|---|---|
| 2,678,878 A | 5/1954 | Stewart | |
| 4,006,186 A * | 2/1977 | Engels | C07C 323/00 564/440 |
| 4,095,970 A | 6/1978 | MacDonald | |
| 2002/0122988 A1* | 9/2002 | Hamamoto | H01M 4/587 429/340 |
| 2005/0256274 A1* | 11/2005 | Voorheis | A63B 37/0003 525/261 |

FOREIGN PATENT DOCUMENTS

GB    1023800 A    3/1966

OTHER PUBLICATIONS

International Search Report and Written Opinion issued in corresponding International Patent Application No. PCT/EP2013/072429 dated Dec. 9, 2013.
Chen et al., "O-substituted benzene (alkyl) sulfenyl benzoic acid as plant growth regulator," Accession No. 2003-222476 Database WPI Thomson Scientific, XP002693541 (2002) abstract.

* cited by examiner

*Primary Examiner* — Tracy Vivlemore
*Assistant Examiner* — Monica Shin
(74) *Attorney, Agent, or Firm* — Morgan, Lewis & Bockius LLP

(57) ABSTRACT

The present invention pertains to plant additives capable of alleviating phosphate starvation symptoms in plants and promoting the growth of phosphate deprived plants. These plant additives are molecules comprising the group of formula.

(II)

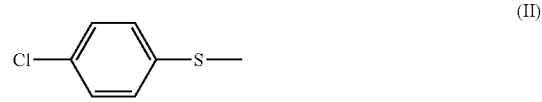

4 Claims, 8 Drawing Sheets

COMPOUNDS FOR ALLEVIATING PHOSPHATE STARVATION SYMPTOMS IN PLANTS

SEQUENCE LISTING SUBMISSION VIA EFS-WEB

A computer readable text file, entitled "SequenceListing.txt" created on or about Mar. 25, 2015, with a file size of about 13 kb contains the sequence listing for this application and is hereby incorporated by reference in its entirety.

The present invention relates to compounds for promoting the growth of a plant, preferably a plant under phosphate limiting conditions. More particularly the present invention relates to compounds for alleviating phosphate (Pi) starvation symptoms in plants.

Inorganic phosphate (Pi) is a crucial plant macronutrient. In most of the soils, this element is present in limiting amounts. Beside, several factors contribute to restrict its availability: (i) assimilation by microbes (ii) capacity to strongly interact with many cations, (iii) and very poor mobility (Shen et al., 2011). As a consequence, Pi is very heterogeneously distributed in soils and can easily be considered as one of the least available plant macronutrients (Raghothama, 1999). To cope with such a situation, plants have developed various adaptations to improve Pi recovery and reduce its consumption.

In cases of phosphate deficiency, plants exhibit drastic changes which increase phosphorus (P) acquisition from soils and improve its use in the plant. Pi starvation leads to morphological modifications such as significant growth reduction, anthocyanin accumulation in the leaves and a modified root architecture to explore P-richer horizons. Phosphate starvation also induces numerous biochemical changes (Raghothama, 1999). Phosphate uptake is enhanced by a combination of an increased number of phosphate transporters, in particular the well known early marker of Pi starvation such as PHT1;4 (Misson et al., 2004) in the plant model *Arabidopsis*, and the secretion of organic acids and enzymes such as phosphatases and nucleases into the rhizosphere.

The reduction of the root system of plants grown in Pi starved medium is a common trait which has been brodely observed. More particularly, in *Arabidopsis thaliana*, Pi starvation conditions effects have been detailed. In response to low (limited) Pi concentrations, important changes are observed favoring the exploration of soil superficial layers, the area of soil containing more Pi (Abel, 2011; Peret et al., 2011). This phenomenon appears to be locally regulated by external Pi concentration, as demonstrated by specific location of Pi supply promoting root development in such area of high Pi concentration (Drew, 1975; Linkohr et al., 2002; Thibaud et al., 2010). Conversely, Pi starvation conditions lead to the reduction of primary root development and to an increase of lateral roots development (Linkohr et al., 2002; Lopez-Bucio et al., 2002; Ticconi and Abel, 2004; Reymond et al., 2006; Sanchez-Calderon et al., 2006). Elements were genetically identified to act on these modifications as LPR1 (Reymond et al., 2006; Svistoonoff et al., 2007), PDR2 (Ticconi et al., 2004) and LPI (Sanchez-Calderon et al., 2006).

Using also *A. thaliana* whole genome Affymetrix gene chip (ATH1), Misson et al. have studied the global gene expression in response to Pi deprivation to quantify the spatio-temporal variations in transcript abundance of 22,810 genes (Misson et al., 2005). The analysis revealed a coordinated induction and suppression of 612 and 254 Pi-responsive genes, respectively. The functional classification of some of these genes indicated their involvement in various metabolic pathways, ion transport, signal transduction, transcriptional regulation, and other processes related to growth and development. In particular, this study demonstrated that several metal transporters were induced in phosphate-deprived plants, and that a significant amount of responsive genes are involved in lipid biosynthetic pathways (Misson et al., 2005).

Pi starvation conditions also lead to metabolic adaptations to increase Pi uptake, to release Pi from organic phosphate pool or to spare and recycle Pi in planta (Arnaud et al., 2010; Tran et al., 2010; Abel, 2011; Peret et al., 2011; Shen et al., 2011). These metabolic modifications are under the control of several elements including in particular the Myb transcription factor PHRJ family, which turns out to be a major regulator for all these responses (Rubio et al., 2001; Bustos et al., 2010; Thibaud et al., 2010).

Plant mutants disconnecting external (lpr1, lpi or pdr2 mutants; for review see Peret et al., 2011; Rouached et al., 2011) or internal Pi concentration (pho1 underexpresser, Rouached et al., 2011) and growth of root or shoot respectively have been discovered. It provides experimental proofs that part of Pi starvation phenotype is under genetic control. Nevertheless nature of this control remains mostly unknown.

Further, in order to increase the productivity of crops, the low (limited) inorganic phosphate (Pi) content of agricultural soils is often supplemented by the application of large quantities of phosphate fertilizers. However, most of these applied inputs remain unavailable for the plants due to organic fixation and inorganic complexation, and the wide use of these fertilizers raises environmental concerns. Indeed, phosphate minerals often contain trace amounts of dangerous substances such as arsenic, cadmium, polonium and uranium, and if no cleaning step is applied after mining, the continuous use of phosphate fertilizers can lead to an accumulation of these elements in the soil.

Moreover, due to an increased demand, the price of phosphate has drastically increased since 2007 (Gilbert 2009).

Therefore, there is a need of plant additives which can alleviate phosphate starvation symptoms in plants and promote the growth of phosphate deprived plants.

By using a chemogenetic screening approach targeting the phosphate transporter PHT1;4 gene in *Arabidopsis*, the inventors have identified a family of compounds named Phosphatins (PTNs) that alleviate or inhibit the expression of the high affinity phosphate transporter PHT1;4.

By using a transcriptomic assay, the inventors have shown that Phosphatins impacted the expression of 40% of the genes regulated by low Pi availabilty. Upon treatment with these compounds, the phosphate transporters PHT1 expression was reduced (around 40%) in Pi limiting conditions that led to a reduced Pi uptake capacity but not to a decrease of Pi content.

The study of the Phosphatins shows that these compounds act at different levels of plant adaptation to Pi starvation. Addition of a Phosphatin to the growing medium induces a decrease in adaptive responses of the plants such as recycling of internal Pi, the ability of Pi import, and the production of starch and anthocyanins.

The inventors have also shown that Phosphatins promote an increase of the growth of the plant grown under phosphate limiting conditions. Indeed, isolated mutants affected in the implementation of responses to Pi starvation, e.g., the Pi transporters pth1;1; pth1;4 mutant (Shin et al., 2004), the phosphatase mutant pap26 (Hurley et al., 2010) and the mutant in glycolipids synthesis mgd3 (Kobayashi et al., 2009), show a reduction in the plant development under phosphate limiting conditions compared to the wild-type *A. thaliana*. Therefore, since the addition of Phosphatins partially inhibit the induction of the Pi import ability, of the Pi recycling and of the phosphatases expression, one could expect that these compounds act negatively on the plant development. However, the inventors have observed opposite results: addition of Phosphatins leads to an overall maintenance of the plant development under phosphate limiting conditions.

The effect of the Phosphatins on the promotion of the growth of a first plant does not arise from a total or a selective herbicide effect on a second plant (e.g., a weed) competing with the first plant.

Accordingly, in a first aspect, the present invention provides the use of a compound of formula I:

A-R$_1$ wherein
A represents a 4-chlorothiophenol group of formula II:

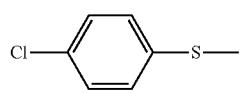

(II)

linked to R$_1$ through its sulfur atom,
R$_1$ represents:
  an hydrogen atom;
  a group A as defined above, linked to the first group A through its sulfur atom;
  an electroattractive group selected from the group consisting of
    O—R, S—R, CO—R, Ar—R, wherein R represents an unsubstituted or substituted, linear or branched C$_1$-C$_6$ alkyl group, a C$_1$-C$_6$ alkoxy group, a C$_1$-C$_6$, alkenyl group, a C$_1$-C$_6$ alkynyl group or an aromatic C$_4$-C$_6$ group, optionally substituted by a group selected from the group consisting of oxygen, sulfur, a halogen atom, NH, NH$_2$ and OH or an unsubstituted or substituted C$_1$-C$_6$ alkyl group and Ar represents a C$_4$-C$_6$ aromatic group
  Ar-A, wherein Ar and A are as defined above
  R$_2$-A, wherein:
    R$_2$ represents an unsaturated C$_4$-C$_6$ cycle, optionally substituted with at least one oxygen atom, preferably two oxygen atoms, said oxygen atom being linked by a double bond to said cycle
  A is a group as defined above, linked to R$_2$ through its sulfur atom and
  a group of formula III:

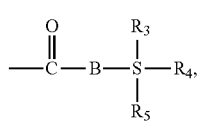

(III)

wherein
  B represents an unsaturated C$_5$-C$_6$ monocycle or a fused bicycle in which each cycle is an unsaturated C$_5$-C$_6$ cycle, optionally substituted with a linear or branched C$_1$-C$_6$ alkyl group,
  R$_3$ and R$_5$ are identical or different, and represent independently a group selected from the group consisting of oxygen, sulfur, a halogen atom, NH, NH$_2$ and OH, preferably an oxygen atom, or an unsubstituted or substituted C$_1$-C$_6$ alkyl group,
  R$_4$ represents a linear or branched unsubstituted or substituted C$_1$-C$_6$ alkyl group;
for promoting the growth of a plant.

The present invention does not encompass the use of a compound of formula I as an herbicide, in particular as a defoliant, a desiccant, an herbage killer, a germination inhibitor or a weed killer.

In a preferred embodiment, said compound alleviates or inhibits in vivo the expression of the PHT1;4 gene encoding the high affinity phosphate transporter PHT1;4 in *Arabidopsis thaliana* (At2g38940). Examples of *A. thaliana* PHT1;4 gene and phosphate transporter PHT1;4 amino acid sequence are referred herein to as SEQ ID NO: 1 and 2 respectively.

Identification of compounds capable of alleviating or inhibiting in vivo the expression of the PHT1;4 gene encoding the high affinity phosphate transporter PHT1;4 in *A. thaliana* can be carried according to the method described in the Examples below or described by Misson et al., 2004.

Preferred compounds of formula A-R$_1$ which can be used according to the present invention are disclosed in the following Table I.

| Name | Formula | R$_1$ |
|------|---------|-------|
| PTN1 | ![structure] | R$_1$ = R$_2$-A wherein R$_2$ is ![structure] A is ![structure] |

-continued

| Name | Formula | $R_1$ |
|---|---|---|
| PTN2 | [structure: indane with C(=O)S-(4-chlorophenyl) and SO₂CH₃ substituents] | $R_1$ = a group of formula III: [structure: indane with acetyl and SO₂CH₃ substituents] |
| PTN3 | [structure: HS-(4-chlorophenyl)] | $R_1$ = H |
| PTN4 | [structure: bis(4-chlorophenyl) trisulfide] | $R_1$ = A —S-(4-chlorophenyl)Cl |

The most preferred compound is PTN1.

Advantageously, the compound according to the present invention is useful for reducing the need for phosphate fertilizer for growing plants.

The term "plant" includes any monocot or dicot plant, such as a plant of the Fabaceae or Brassicaceae family, in particular *Medicago sativa* (Alfalfa).

In another embodiment, said plant is grown under phosphate limiting conditions.

As used herein, the term "under phosphate limiting conditions" means under low phosphate conditions, i.e., under a content of phosphate that is not optimum for the growth of the plant.

In a second aspect, the present invention provides a plant additive composition comprising:
 a compound of formula I as defined above and
 a formulation adjuvant, such as a carrier, a solvent or a surface-active agent.

By "plant additive composition" is herein meant any kind of soil additive, soil amendment, fertilizer or soil conditioner, which can of course be used to modify a soil, but also in hydroponic cultures.

More particularly, said plant additive composition is a composition for promoting plant growth and/or for alleviating Pi starvation symptoms.

The plant additive composition according to the present invention is not intended for use as an herbicide, in particular as a defoliant, a desiccant, an herbage killer, a germination inhibitor or a weed killer.

The plant additive composition can be a liquid or solid (typically granulated or powdered) composition, such as dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oil dispersions, suspoemulsions, capsule suspensions, emulsifiable granules, soluble liquids, water-soluble concentrates (with water or a water-miscible organic solvent as carrier), or impregnated polymer films.

In a particular embodiment, the plant additive composition further comprises at least one primary nutrient selected from the group consisting of nitrogen and potassium, and/or at least one secondary nutrient selected from the group consisting of calcium, magnesium, sodium and sulfur, and/or at least one micronutrient selected from the group consisting of boron, cobalt, copper, iron, manganese, molybdenum and zinc.

Advantageously, said plant additive composition comprises a compound of formula I as defined above and at least the 2 primary nutrients as defined above.

Advantageously, said plant additive composition comprises a compound of formula I as defined above and at least the 2 primary nutrients and the 4 secondary nutrients as defined above.

Advantageously, said plant additive composition comprises a compound of formula I as defined above, nitrogen, potassium, calcium, magnesium, sodium, sulfur, boron, cobalt, copper, iron, manganese, molybdenum and zinc.

Advantageously, a liquid plant additive composition comprises a solvent such as a polar water-soluble solvent, a micelle or a surfactant.

In a third aspect, the present invention provides a method for promoting the growth of a plant, comprising adding to the growing medium or soil on which said plant is grown, a compound of formula I as defined above, or a plant additive composition comprising a compound of formula I as defined above and a formulation adjuvant as defined above.

The method according to the present invention is not intended for promoting the growth of a plant by inhibiting the growth of another plant (e.g., a weed).

Preferably, said plant is grown under phosphate limiting conditions.

The growing medium includes liquid, semi-solid or solid medium suitable to support the growth of a plant. By way of example, it can be a mineral nutrient solution or an inert material such as heydite, clay pellets, perlite, vermiculite or rockwool.

Advantageously, the growing medium contains the nutrients required to support the growth of the plant.

In a fourth aspect, the present invention provides the use of a compound of formula I as defined above for preparing a plant additive composition as defined above useful for promoting the growth of a plant.

Preferably, said plant is grown under phosphate limiting conditions.

In a fifth aspect, the present invention provides the use of a compound of formula I as defined above for screening compounds affecting (i.e., modifying) the establishment of the response of a plant to phosphate starvation.

Preferably, said plant is grown under phosphate limiting conditions.

As used herein, "the establishment of the response of a plant to phosphate starvation" means the morphological and metabolism adaptation or modification of a plant grown under phosphate limiting conditions.

In an embodiment of this aspect of the present invention, a genetic approach can be used, wherein it is carried out a screen for plant mutants altered in their growth response to a compound of formula I as defined above.

Foregoing and other objects and advantages of the invention will become more apparent from the following detailed description and accompanying drawing. It is to be understood however that this foregoing detailed description is exemplary only and is not restrictive of the invention.

Figure 3:
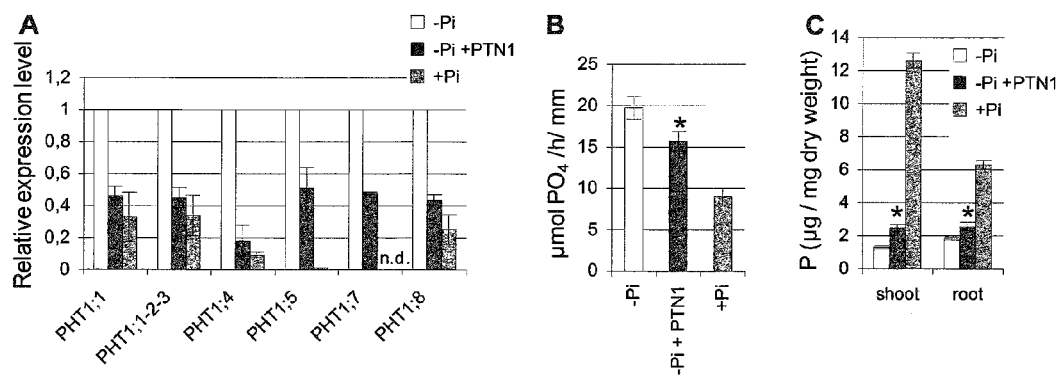

FIG. 3 shows that PTN1 modulated Pi uptake. (A) Impact of PTN1 treatment on various PHT1 transcript level. Measures were performed using qPCR experiments on root mRNA extracted from plants treated or not with 40 µM (−Pi: white bars; −Pi+PTN1: dark grey bars; +Pi: light grey bars). (B) Impact of PTN1 on phosphate influx. (C) Impact of PTN1 on total phosphorus content. Measures were performed using Inductively Coupled Plasma (ICP) assays. n.d. for not detected expression. Asterisks represent significant difference between −Pi and −Pi+PTN1 (student's t test, P<0.01). 7-day-old plantlets have been used for various experiments.

Figure 4:
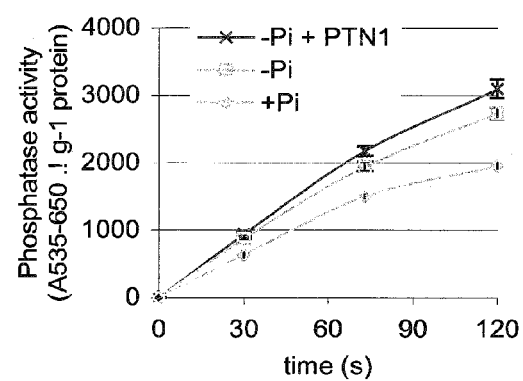

FIG. 4 shows that PTN1 modulation of phosphatases expression did not impact the phosphatase activity by measuring the impact of PTN1 on the phosphatase activity. Assay of the activity on root samples of 7-days-old plants grown on −Pi, −Pi+PTN1 40 µM or +Pi conditions.

Figure 5:
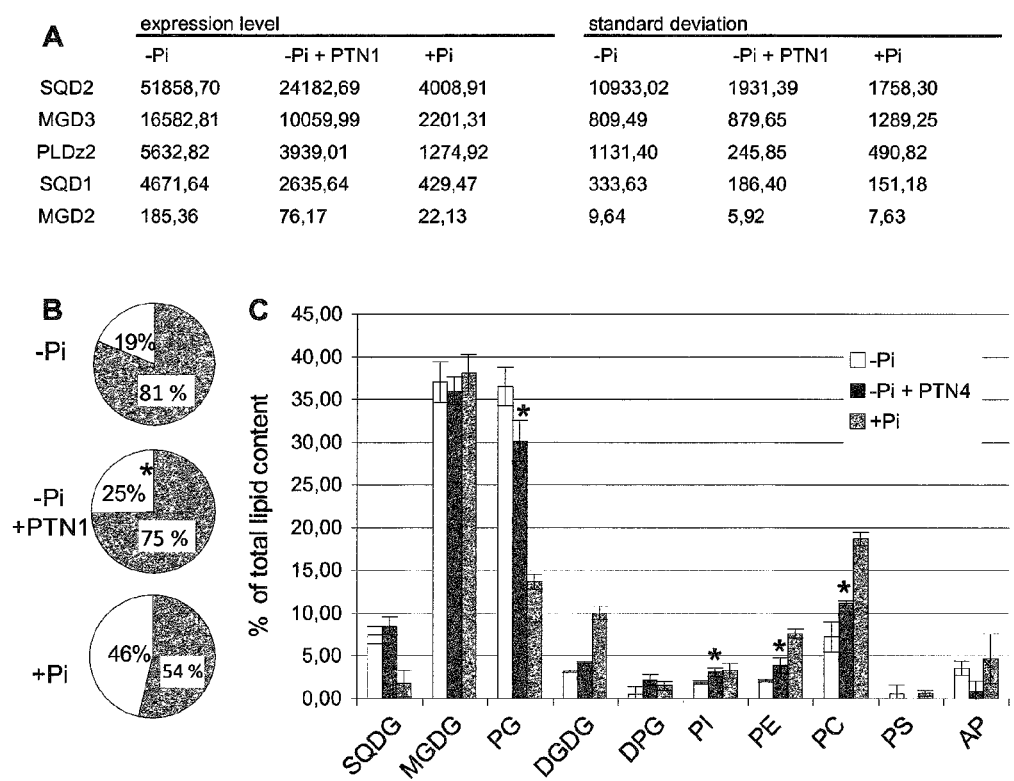

FIG. 5 shows that PTN1 reduced metabolic stress during phosphate starvation. (A) Measure of transcript level (by qPCR) of genes involved in the lipids synthesis for plants grown on −Pi, −Pi+PTN1 (40 µM) and +Pi during 14 days. (B) Balance between phospholipids (white sectors) and glycolipids (grey sectors) for plants grown on −Pi, −Pi+PTN1 and +Pi media. (C) Lipid composition of wild-type plants grown on low Pi (white bars), low Pi+PTN1 (dark grey bars) and high Pi (light grey bars). Total lipid was extracted from the aerial part of 10-day-old plants. Asterisks represent significant differences between −Pi and −Pi+PTN1 (student's t test, P<=0.01).

Figure 6:
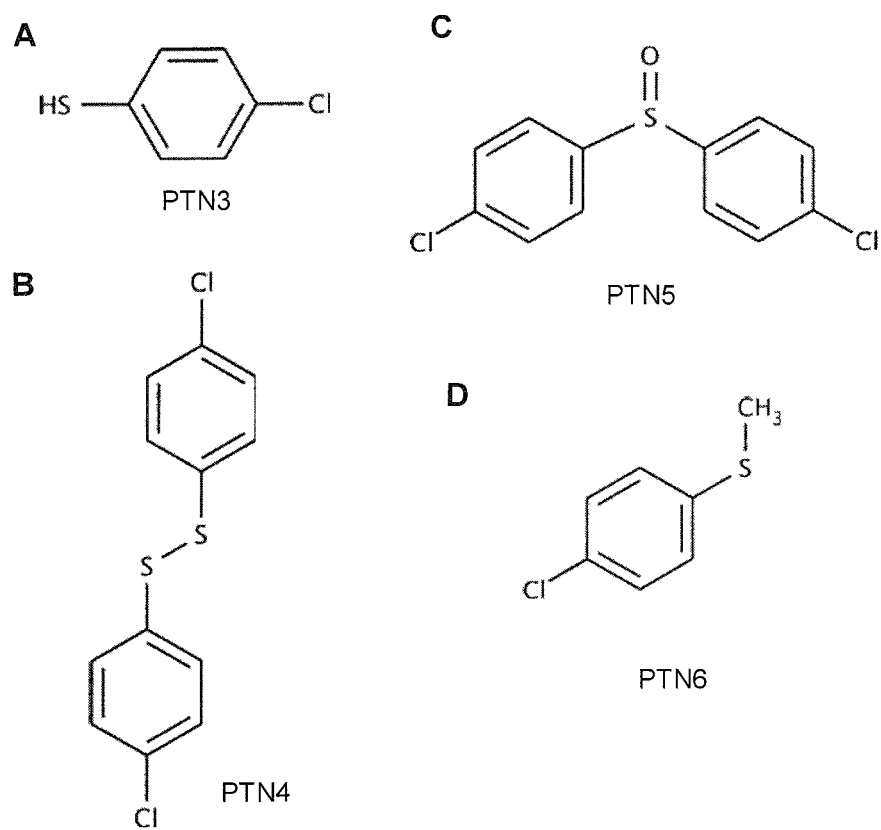

FIG. 6 shows the structures of compounds tested for their effects on the primary root growth of wild-type (WT) seedlings (A, PTN3; B, PTN4) Active compounds. (C,D) Inactive compounds.

Figure 7:
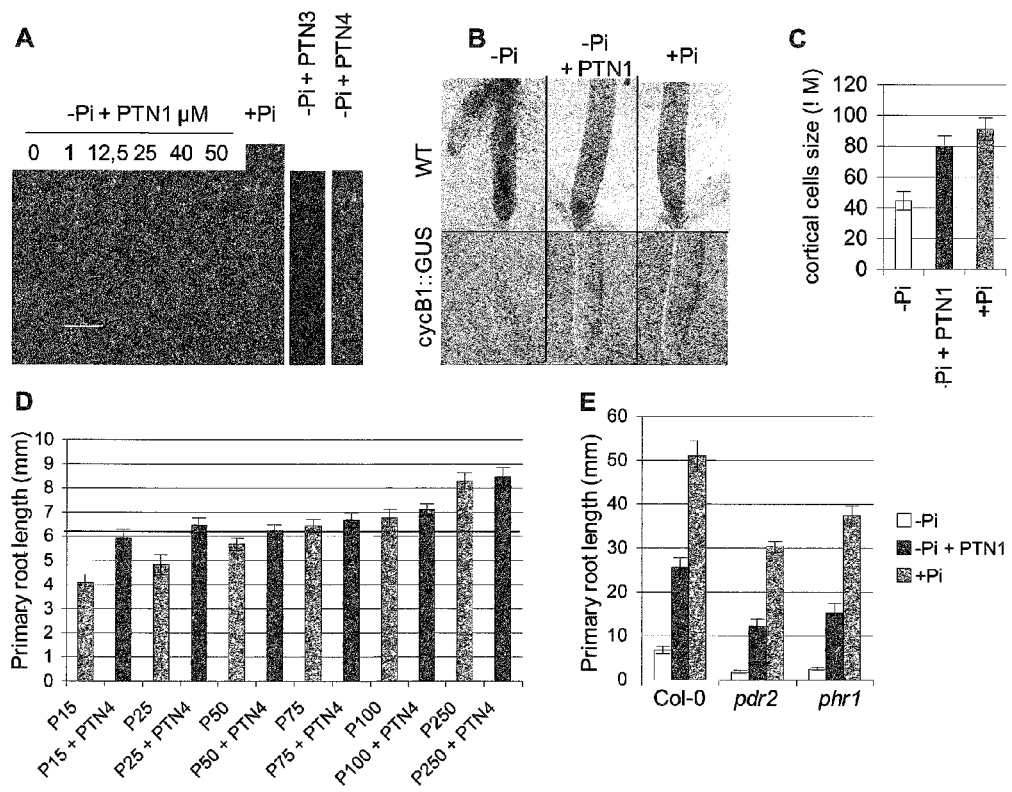

FIG. 7 shows that PTNs unlocked the primary root arrest. (A) Identification of optimal PTN1 level to suppress Pi starvation effect on root growth. Similar effect can also be observed with PTN3 and PTN4 using respectively 100 µM or 10 µM application (B) Analysis of cell cycle using cycB1::GUS marker. Pictures of root tip of wild type (top) and cycB1::GUS (bottom) grown on −Pi, −Pi+PTN1 40 µM or +Pi conditions, after GUS staining. (C) Measure of cortical cell size on WT plantlets grown on the different medium (PTN4 10 µM). (A,B,C) 7-day-old plantlets have been used for various experiments. (D) Effect of Pi concentration on PTN effect on the primary root length. For the measure of the primary root growth, plants were grown during 5 days on Pi rich medium and transferred on various conditions tested during 24 hours (PTN4 10 µM). The line (between 6 an 7 mm) shows the maximum gain of growth conferred by PTN1 presence. (E) Effect of PTN treatment on mutants affected in the root architecture response to Pi starvation. Measure of the primary root growth of WT plants, pdr2 and phr1 mutants 9 days after germination on the different medium (PTN1 40 µM).

Figure 8:
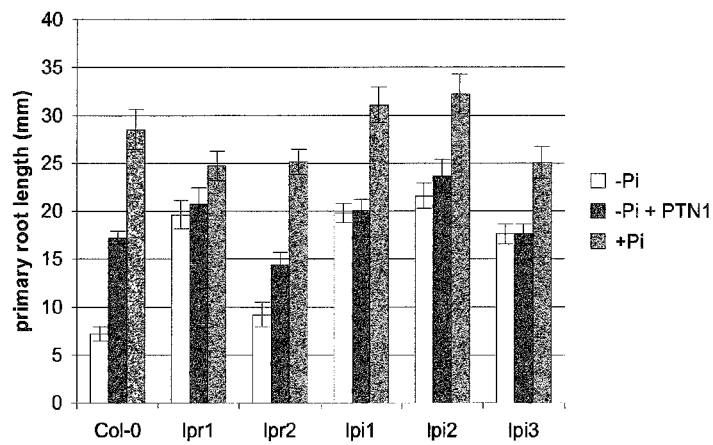

FIG. 8 shows that PTN1 addition did not impact the primary root growth of Pi insensitive mutants, by measuring the impact of PTN1 on the primary root growth of mutants altered in their root sensitivity to Pi starvation. Measure of the primary root growth of 7-days-old plants grown on −Pi, −Pi+PTN1 40 µM or +Pi conditions.

Figure 9:
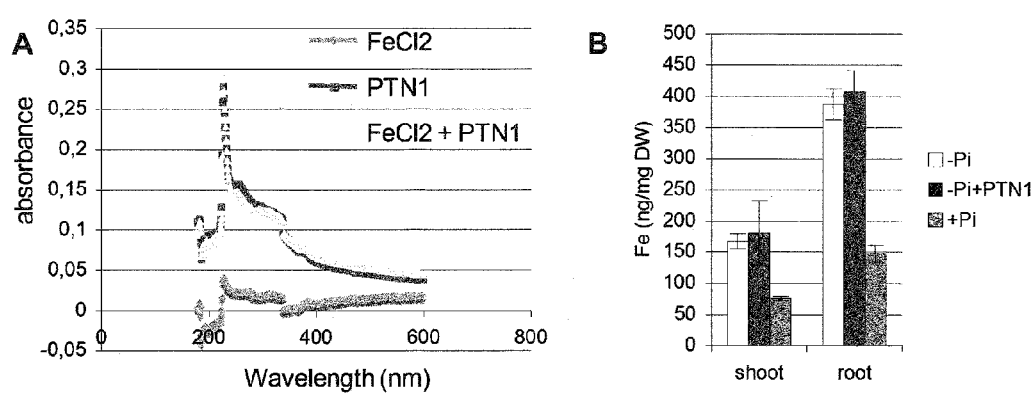

FIG. 9 shows that PTN1 effects were independent of Fe signaling using a test of the importance of the iron for PTN1 effects. (A) Curves of optical density of PTN1 at 40 µM, FeCl2 at 10 µM and 40 µM PTN1+ 10 µM FeCl2. (B) Fe content assay by ICP of plantlets grown on −Pi, −Pi+PTN1 40 µM and +Pi.

Figure 10:
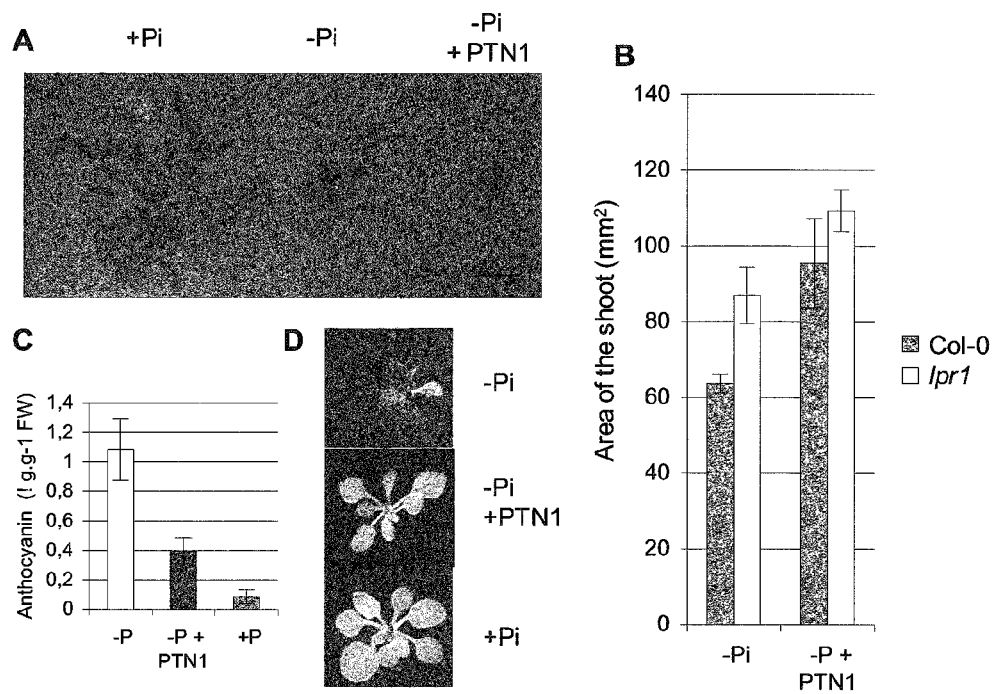

FIG. 10 shows that PTN1 unlocked the general growth during a Pi starvation. (A) Effect of PTN1 addition on leaves growth. Shoot of 28-days-old plants grown on +Pi, −Pi or −Pi+PTN1 conditions. (B) Measure of the shoot area of Col-0 and lpr1 mutant, performed after 28 days of growth. (C) Anthocyanins content for plants grown on −Pi, −Pi+PTN1 or on +Pi. (D) Starch content revealed by shoot staining of with lugol.

Figure 11:
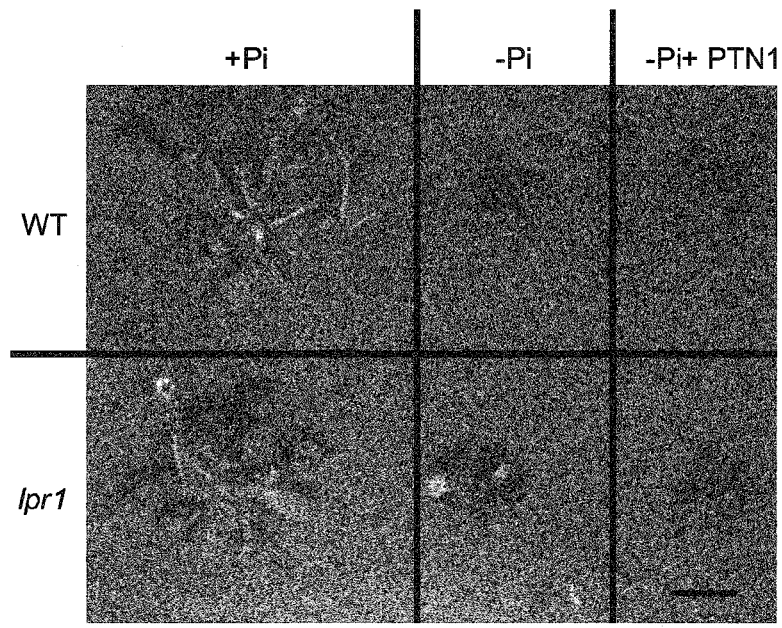

FIG. 11 shows that PTN1 addition led to an increase of the growth of the lpr1 mutant by measuring the impact of the lpr1 mutation on the shoot growth in Pi starvation conditions. Picture of WT and lpr1 28-days-old plants grown on −Pi, −Pi+PTN1 40 µM or +Pi conditions. Scale: 1 cm.

Figure 12:
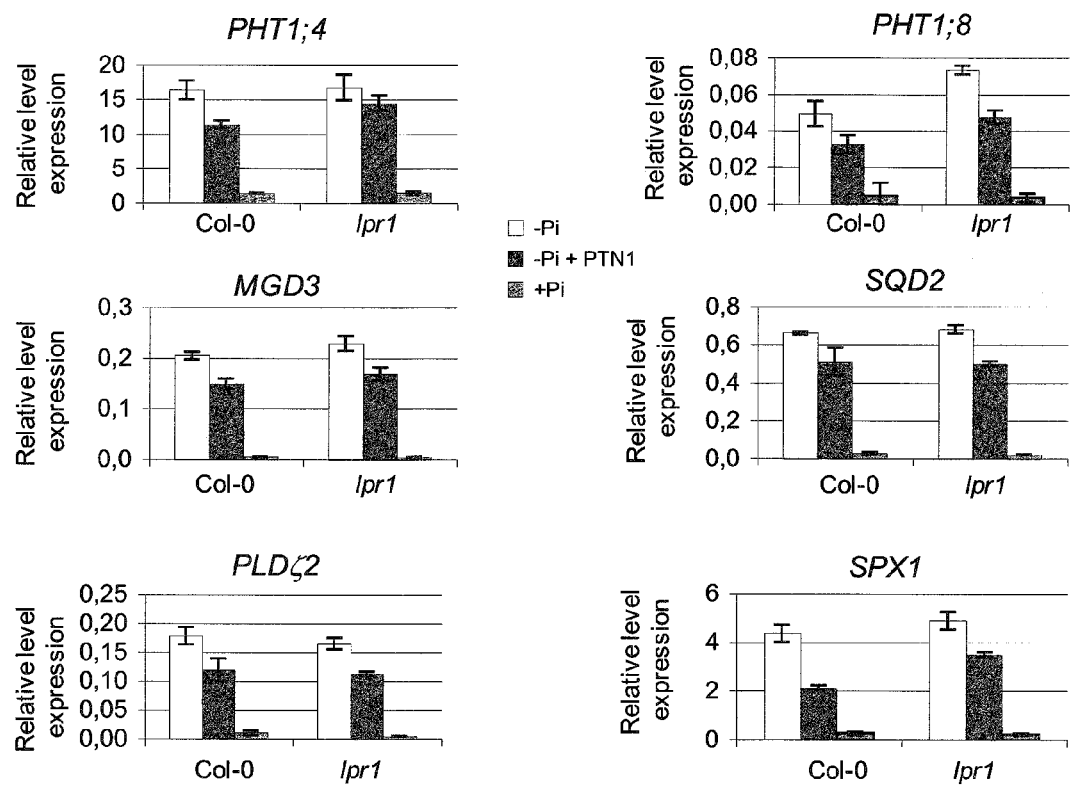

FIG. 12 shows that the maintain of the primary root growth did not impact the gene regulation using a qPCR assay of genes regulated by Pi starvation in the WT Col-0 and the mutant lpr1 14 days-old plants. Same expression patterns were observed between the two lines.

EXAMPLE: IDENTIFICATION Of PHOSPHATIN, A COMPOUND ALLEVIATING PHOSPHATE STARVATION RESPONSE In *ARABIDOPSIS*

1) Material & Methods
Plant Materials and Growth Conditions

A "chemical genetics" approach has been carried out to isolate compounds that inhibit the phosphate (Pi) response in *Arabidopsis thaliana*. Compounds were screened for their ability to inhibit the expression of a phosphate starvation marker, namely the high affinity Pi transporter PHT1,4 gene. For the screening, the *A. thaliana* pht1;4-1 line (ecotype Wassilewskija) was chosen (Misson et al., 2004). It contains a T-DNA construct inserted into Pht1;4 gene creating a transcriptional fusion with a GUS reporter gene. For phenotypic analyses, *A. thaliana* Columbia and various lines derived from this ecotype were used. They are either transgenic lines expressing reporter gene as cycB1::GUS (Colón Carmona et al., 1999), MGD3::LUC, PHT1;4::LUC, At1g73010::LUC or various mutants affecting root response to low Pi such as: pdr2 (Ticconi et al., 2004), lpr1, lpr2 (Svistoonoff et al., 2007), lpi1, lpi2 and lpi3 (Sanchez-Calderon et al., 2006).

For in vitro analyses, seeds were surface-sterilized and sown in vitro on square Petri plates with solid MS/10 medium (0.15 mM $MgSO_4$, 2.1 mM $NH_4NO_3$, 1.9 mM $KNO_3$, 0.5 or 0.005 mM $NaH_2PO_4$, 0.3 mM $CaCl_2$, 0.5 µM KI, 10 µM Fe, 10 µM $H_3BO_3$, 10 µM $MnSO_4$, 3 µM $ZnSO_4$, 0.01 µM$CuSO_4$, 0.01 µM $CoCl_2$, 0.1 µM $Na_2MoO_4$, 2 µM EDTA, 0.03 µM thiamine, 0.24 µM pyridoxine, 0.4 µM nicotinic acid, 55 µM inositol, 14 mM MES (pH 5.7)), 0.5% sucrose and 0.8% agar. In the Pi deficient medium, NaCl (0.5 mM) was used to replace the equivalent amount of sodium provided by $NaH_2PO_4$. For controls of the effects of the compounds, 1% of DMSO (Dimethyl sulfoxid, SIGMA, 472301), solvent for the tested compounds, was added. After 2 days at 4° C., the plates were placed in a vertical position and plants were grown in a culture chamber under a 16 h light/8 h dark regime (24/21° C., 150 µE $m^{-2}s^{-1}$). For 4 weeks culture, large plates (24×24 cm) were placed in a horizontal position. Root architecture and aerial part area were quantified using program ImageJ.

Chemical Genetics Screening

For the screening, the LATCA collection of 3600 biologically active compounds (Zhao et al., 2007) was used at a final concentration of 25 µM in 1% DMSO. Four to five *Arabidopsis* seeds of pht1;4-1 (Misson et al., 2004) reporter line were sown in 96-well plates containing 100 µL liquid MS/10 medium with 500 µM of Pi at pH 5.7. After 2 days at 4° C., plants were grown for five days in a culture chamber under a 16 h light/8 h dark regime (24/21° C., 150 µE $m^{-2}s^{-1}$). Medium was then replaced by MS/10 with only 5 µM Pi and the tested compounds were added to the 96-well plates. Positive and negative controls were included by incubating seedling in MS/10 solutions containing 1% DMSO and completed with 5 or 500 µM Pi respectively (giving rise to −Pi or +Pi medium). Five days later, plantlets were analysed by GUS staining to assay the activity of the reporter gene inserted in pht1;4 gene. 100 µL of GUS staining solution were added in each well and plates were incubated 3 hours at 37° C. Then, plates were analysed using a MZ16 stereomicroscope (Leica microsystems, Germany).

GUS Staining

The GUS activity was detected as previously described by Jefferson et al. (1987), using a GUS staining solution containing 50 mM sodium phosphate buffer pH 7.0; 0.01% Triton X-100, 1 mM $K_3Fe(CN)_6$, 1 mM $K_4Fe(CN)_6$, 1 mg/ml 5-bromo-4-chloro-3-indolyl B-D-glucuronide (X-Gluc). For cycB1::GUS staining, plants were incubated 6 hours at 37° C.

Bioluminescence Quantification

Plants carrying the luciferase gene marker were analysed with the Bioluminescence Imaging System LV200 (Olympus, Japan) and PS-25 camera (Andor, US). Signals were quantified with ImageJ software.

Transcriptome Analysis and Quantitative Real-Time Polymerase Chain Reaction

Plant RNA was extracted with the RNeasy kit (QIAGEN, France). For transcriptome data, RNA were analysed by the CATMA technology (Complete *Arabidopsis* Transcriptome Microarray). For qPCR, poly(dT) cDNA were prepared from 500 ng total RNA with Superscript III reverse transcriptase (Invitrogen, France) and analysed on a LightCycler 480 apparatus (Roche Diagnostics, France) with the SYBR Green I Master kit (Roche Diagnostics, France) according to the manufacturer's instructions. Targets were quantified with specific primer pairs designed with Primer3 website (http://frodo.wi.mit.edu/primer3/) (see Table II below). Biological triplicates were performed for all experiments. Expression levels were normalized using At2g16600, At3g04120, At1g35160 and At1g32050 genes.

TABLE II

List of primers used for RTqPCR

| AGI | forward | reverse | amplicon size |
|---|---|---|---|
| PHT1; 1 | CAACTTGAGGAGGCGTTGA (SEQ ID NO: 3) | GGTTTTGGTTGGGATTTGG (SEQ ID NO: 4) | 234 |
| PHT1; 1_2_3 | GACTACCCACTTTCTGCCACCAT (SEQ ID NO: 5) | CTTTCCTCAAGCTCGATATCTGT (SEQ ID NO: 6) | 384 |
| PHT1; 4 | CCTCGGTCGTATTTATTACCACG (SEQ ID NO: 7) | CCATCACAGCTTTTGGCTCATG (SEQ ID NO: 8) | 239 |

TABLE II-continued

List of primers used for RTqPCR

| AGI | forward | reverse | amplicon size |
|---|---|---|---|
| PHT1;5 | CGTTGTTGATGCTTGCTTGT (SEQ ID NO: 9) | CTACCGGAATTTGCCACAGT (SEQ ID NO: 10) | 157 |
| PHT1;7 | TCCCTCATTGTTTTGGGTGT (SEQ ID NO: 11) | GTTCGTTCTCACCGGACATT (SEQ ID NO: 12) | 106 |
| PHT1;8 | AAACGCCACCAAGAATCAAG (SEQ ID NO: 13) | TCCCGGCTAGGTTTAGGTCT (SEQ ID NO: 14) | 180 |
| MGD2 | ACAAGAAATTGGCATCTGCAT (SEQ ID NO: 15) | TGGTCCAGCTTTTGTGATGA (SEQ ID NO: 16) | 125 |
| MGD3 | AGAGGCCGGTTTAATGGAGT (SEQ ID NO: 17) | CATCAGAGGATGCACGCTAA (SEQ ID NO: 18) | 122 |
| SQD2 | TACCTGAAGCTCGGATTGCT (SEQ ID NO: 19) | TGTGAGAGTTCATCGCCTTG (SEQ ID NO: 20) | 118 |
| SQD1 | AGCTTGGGCTAGACGTGAAA (SEQ ID NO: 21) | AGGCTCAAGTCCAAGTTCCA (SEQ ID NO: 22) | 110 |
| PLDz2 | TGCATTGCTGGAGACAAAAG (SEQ ID NO: 23) | TTTTGAAGCCGTTTCTTGCT (SEQ ID NO: 24) | 114 |

Quantification of Macro- and Microelements, Anthocyanins and Lipids

For the quantification of ions content, 50 mg of dry weight of each sample were mineralized in 14% HNO3 using a MarsX microwave system (CEM) for the determination of macro- and microelements by inductively coupled plasma optical emission spectrometry (ICP OES Vista MPX, Varian). Biological triplicates were performed for all experiments.

Lipids and anthocyanins were analyzed as previously described by Jouhet (2003) and Ticconi (2001).

Phosphate Uptake Experiments

Phosphate uptake experiments were performed as previously described by Narang et al. (2000). 24 seedlings per conditions were incubated separately in a phosphate incubation solution containing $^{33}PO_4$ (5 mM MES, 0.1 mM $CaCl_2$, 20 µM $KH_2PO_4$, 0.15 µCi/ml $^{33}PO_4$) for 2 h. After incubation in the uptake solution, plantlets were transferred to a chilled desorption medium (5 mM MES, 0.1 mM $CaCl_2$, 1 mM $KH_2PO_4$) for 2 h at 4° C. Then, the seedlings were dried in scintillation vials at 60° C. overnight. An amount of 2 ml of scintillation cocktail (InstaGel, PerkinElmer, Wellesley, Mass., USA) was added and the radioactivity was measured with a scintillation analyzer (TRICARB, Packard instrument company). The amount of phosphate absorbed during the experiment was calculated and normalized per cm of root.

Protein Extraction and Phosphatase Activity

Soluble proteins were extracted with 50 mM TRIS pH 7.4 and 1 mM DTE (1,4-Dithioerythritol, Sigma, 6892-68-8). The protein concentration was determined by the Bradford methods, using albumin from bovine serum (BSA, Sigma, 9048-46-8) as a standard. The phosphatase activity in solution was determined as previously described by Kolari and Sarjala, (1995), by measuring the release of nitrophenol from 0.6 mM p-nitrophenylphosphate in 50 mM sodium acetate pH 5. Reactions were incubated at 30° C. for 30, 60 and 90 mM and were stopped with 10% of Na2CO3, after which the absorbance at 405 nm was measured.

Starch Staining

Starch staining was performed according to Zakhleniuk et al. (2001). Aerial part of plants was placed 6 h in EtOH 90% before to be iodine stained for 30 min in lugol (lugol solution; Sigma, France) and washed several times in water.

Statistical Analyses

Data were analysed by student's t test. Asterics represent means that were statistically different at $P<0.05$ as mentioned.

2) Results

Identification of Compounds Inhibiting the Low-Phosphate Induced PHT1;4 Gene

The commercially available LATCA library (UC Riverside) containing 3,580 biologically active compounds (Zhao et al., 2007) was screened at 25 µM to identify compounds inhibiting the expression of PHT1;4. This gene is strongly induced by Pi starvation as revealed by previous studies (Karthikeyan et al., 2002; Misson et al., 2004; Misson et al., 2005). The *A. thaliana* line used for the screen, pht1;4-1, contained a GUS transcriptional fusion with the endogenous PHT1;4 gene allowing to monitor its expression (Misson et al., 2004). For the screen, seedlings were germinated and grown during the first five days on Pi rich medium (+Pi, 500 µM) before transfer on Pi limiting medium (−Pi, 5 µM) with the tested compounds for five more days. Then, GUS staining was performed to monitor the expression of PHT1.4.

Figure 1:
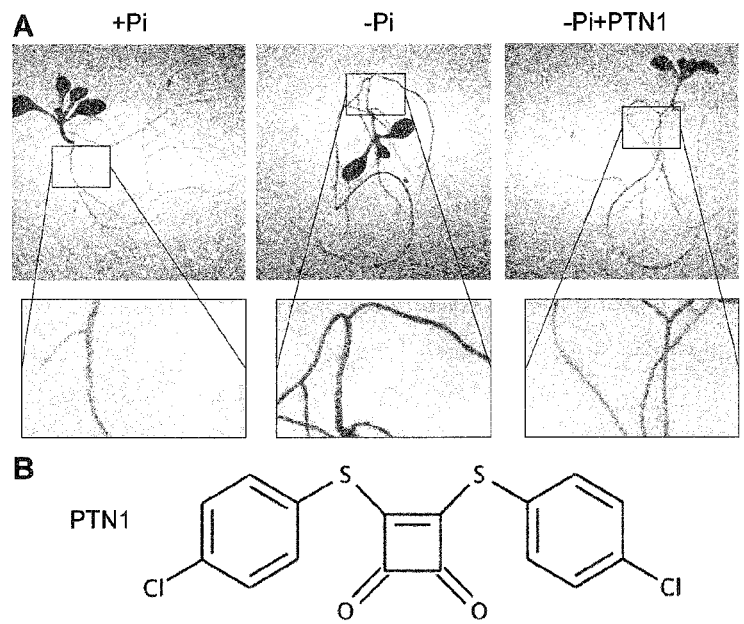
FIG. 1 shows the identification of compounds altering PHT1;4 expression. (A) Presentation of the screen used to identify PTN compounds. GUS staining of pht1;4-1 plantlets germinated and grown 5 days on +Pi (500 µM) and transferred for 5 days on +Pi+DMSO, −Pi (15 µM) +DMSO or on −Pi+phosphatin1 (PTN1 25 µM). (B) Structure of PTN1.
Figure 2:
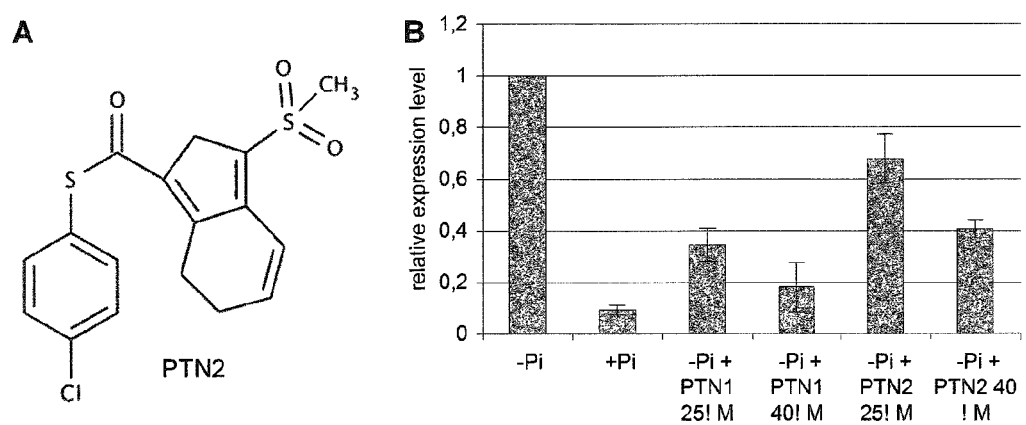
FIG. 2 shows that phosphatins (PTNs) reduced the PHT1;4 expression in a dose dependant manner. (A) Structure of Phosphatin 2 (PTN2). (B) Impact of PTN1 and PTN2 treatment on PHT1;4 transcript level. Measures were performed using qPCR experiments on root mRNA extracted from plants treated or not with the PTNs.

This screen identified 21 compounds that partially (alleviate) or totally inhibit PHT1;4::GUS expression. For most of them the reduced expression of the marker turns out to result from the presumably toxic effects of the tested compound (revealed by growth arrest of the plantlets). For two compounds the reduced expression of the reporter gene was not explained by toxicity (see below). Commercially available compounds MWP00917 and KM03772 in the Maybridge library were named Phosphatin1 (PTN1) and Phosphatin2 (PTN2) respectively (see FIGS. 1 (A), (B) and FIG. 2 (A)). Both compounds assayed on PHT1;4 acted in a dose dependant manner and PTN1 was found twice more efficient than PTN2 (see FIG. 2 (B)) and was therefore selected to pursue experiments.

PTN1 Reduced Gene Expression Modulation by Phosphate Starvation

To investigate on a wider scale the putative Phosphatin1 effect, a transcriptional analysis of the global genome was performed using the CATMA technology (http://www.catma.org/, URGV, France). It was compared transcript expression in roots of 14-days-old plantlets, grown in −Pi, −Pi+PTN1 or +Pi.

When compared to the −Pi conditions, the +Pi conditions modulated the expression of 1062 genes: 783 repressed and 279 significantly induced (see Table III below), whereas PTN1 modulated 2667 genes: 1001 induced and 1666 repressed (based on statistical analysis, Bonferroni test <0.05, with more than two fold change) (see Table ff1).

Table III: Comparison of PTN1 treatment and phosphate supply on global transcriptomic analysis. For this analysis, 14-days-old WT root samples of plants grown on −Pi, −Pi+PTN1 (40 µM) and +Pi were used. Data are expressed as ratio values between +Pi and −Pi or −Pi+PTN1 and −Pi respectively. Number of genes regulated by Pi and PTN1 addition and percentage of genes regulated by +Pi also regulated by PTN1 (selected genes exhibited at least two fold change difference with −Pi control and statistical Bonferroni test <0.05) are shown.

|  | 1666 genes repressed by PTN1 | 1001 genes induced by PTN1 |
| --- | --- | --- |
| 783 genes repressed +Pi/−Pi | 316 (40.3%) | 30 (3.8%) |
| 279 genes induced +Pi/−Pi | 11 (3.9%) | 115 (41.2%) |

Interestingly, a broad part of genes whose expression was modulated by +Pi turns out to be modulated in a similar way by PTN1 addition in −Pi conditions (40% and 41% respectively for repressed or induced transcripts (Table III). Only very few genes (around 4%) were found significantly de-regulated by PTN1 addition in an opposite way when compared with +Pi treatment (Table III). For genes modulated by PTN1 and not by Pi supply, analyze with Genevestigator (https://www.genevestigator.com) also pinpoint links with phosphorus metabolic process and phosphate-containing compound metabolic process. This transcriptomic result indicated that PTN1 overall mimicked the addition of Pi in the growth medium.

In order to refine this transcriptomic analysis, it was looked whether PTN1 modulated the expression of a particular class of genes, as defined by Thibaud et al. (2010) according to their local or long distance regulation by phosphate. Among the so-called systemic genes that were repressed or induced by Pi in these experimental conditions, respectively 65% and 55% were also regulated by PTN1 in the same direction as Pi. Many of them have predicted function involved in Pi recycling, recovery or transport. Among the so-called local genes that were repressed by Pi in these experimental conditions, 45% were also repressed by PTN1. These genes are transcription factors, metal-related genes, linked to hormone or stress-related response, or else involved in the development.

All together this analysis revealed that PTN1 mimicked Pi in the regulation of many genes involved in different metabolisms, and there was no specificity with respect to the local or long distance regulation. The physiology of the plants treated by Phosphatin was investigated to measure the impact of the modifications triggered by PTN1 addition.

PTN Reduced the Metabolic Adaptation Triggered by Pi Starvation

The reduced level of expression of PHT1;4 as assayed by GUS staining was confirmed by qPCR experiments in WT seedlings (see FIG. 3 (A)) and by transcriptomic analysis reported above. This last experiment revealed also the down regulation of other PHT1 genes such as PHT1;5 and PHT1;8. All these genes have been reported to be down regulated by Pi presence in the past (Mudge et al., 2002; Misson et al., 2004; Shin et al., 2004; Misson et al., 2005; Nagarajan et al., 2011). To investigate further the impact of PTN1 on the PHT1 genes, the expression of several additional members of this family were tested. As shown in FIG. 3 (A), PTN1 strongly reduced (at least 50%) the impact of Pi starvation on the level of induction of all these transcripts. Since the PHT1 was the main Pi-influx transporters during Pi-starvation and that the expression of several PHT1 genes was less induced by −Pi in seedlings treated with PTN1, it was tested whether Pi uptake was also reduced by PTN1. Pi uptake experiments and analysis of phosphorus content were performed to measure the impact of these modifications on Pi import. The Pi influx capacity is higher in Pi-starved seedlings (FIG. 3 (B), compare −Pi with +Pi). PTN1 reduced (by 25%) also the Pi uptake capacity. Seedlings treated with PTN1 contained higher amounts of phosphorous than the −Pi control (+90% and +40% in shoot and leaves respectively, FIG. 3 (C)).

Another way to recover Phosphorus in the medium for plants is to secrete acid phosphatase (PAP) to mobilize putative organic Pi present in the growth medium. As already described (del Pozo et al., 1999), it was observed that Pi-starvation stimulated transcription of the PAP12, PAP17 and PAP22 genes as well as the phosphatase activity (FIG. 4). However, although PTN1 reduced the expression level of these three PAP genes, the phosphatase activity was not altered (FIG. 4).

The lipid composition was also checked. The conversion of phospholipids to galactolipids and sulfolipids is a well-established response to Pi starvation (Dormann and Benning, 2002; Nakamura et al., 2009; Moellering and Benning, 2010; Nussaume et al., 2011). This lipid conversion relies on several enzymes such as SQD2, MGD3, PLDz2, SQD1 and MGD2 whose gene expression is induced during the starvation (Dormann and Benning, 2002; Nakamura et al., 2009; Moellering and Benning, 2010; Nussaume et al., 2011). The transcriptomic analysis showed that PTN1 down regulated several of these genes including PLDζ2 and MGD3. This result was confirmed and extended by qPCR showing that PTN1 repressed the expression of genes SQD2, MGD3, PLDz2, SQD1 and MGD2 (see FIG. 5 (A)).

It was then determined whether lipid composition was altered in seedlings treated by PTN1. As shown in the FIG. 5 (B), the ratio of phospholipids onto glycolipids (galacto and sulfolipids) is 19%/81% and 46%/54% in Pi-rich versus Pi-starved seedlings, respectively. Interestingly, in seedlings grown on a −Pi medium containing PTN1, this ratio was 25%/75%; this was intermediate between the two controls. Therefore, PTN1 significantly reduced the effect of Pi-starvation on the overall lipid composition.

The remodelling of glycerolipids consists into a hydrolysis of several phospholipids (phosphatidylcholine (PC), phosphatidylinositol (PI) and phosphatidylethanolamine (PE)) and into an increase of the synthesis of galactolipids (digalactosyldiacylglycerol or DGDG). As shown in FIG. 5 (C), −Pi seedlings contained much less PC and PE than +Pi seedlings, and PTN1 partially reverted the effect of −Pi (FIG. 5 (C)). Conversely, the DGDG content, which increased in Pi-starved plants, was reduced by 27% by PTN1 (FIG. 5 (C)). These biochemical analyses demonstrated that PTN1 reduced the phospholipids conversions of Pi-starved plants, in accordance with the transcriptomic results.

PTN1 Promoted Root Growth of −Pi Seedlings

As reported above, PTN1 reduced significantly several of the adaptative mechanisms known to help the plant to cope with sparse Pi availability (i.e. increase of Pi uptake and phospholipids recycling). Thus, one can expect that PTN1 reduced also plant growth by inhibiting these adaptative responses. Indeed, the loss of function mutant of PHR1, a transcription factor regulating many of the low-Pi responses (Rubio et al., 2001; Bustos et al., 2010; Thibaud et al., 2010, displays a marked growth reduction (Bustos et al., 2010). The effects of PTN1 and PTN4 (an active structural analogue of PTN1; see FIG. 6) was therefore monitored on plant growth. Unexpectedly and in contrast to what it was expected, PTN1 turned out to promote the primary root growth in a dose dependent manner (FIG. 7 (A)). Like for the inhibition of PHT1;4, a maximum effect of PTN1 was observed at 40 nM.

Importance of 4-Chlorothiophenol Motif

This impact on root growth of PTN compounds provided an easy quantitative screen to monitor PTN effects on plants. It was therefore used to test various analogues of PTN1 in order to try to identify the active motif present in PTN1 structure. Both PTN1 and PTN2 presented a common structure composed of a benzene aromatic cycle with sulfur and chlorine residue in para disposition. Such structure (4-chlorothiophenol named PTN3) was commercially available and could therefore be tested (see FIG. 6 (A)). It sustained also the primary root growth, and repressed PHT1;4 expression but requested higher concentration (100 µM; FIG. 7 (A)). Several other analogues containing similar putative active motif were also tested for their inhibitor activity of PHT1;4 expression and their effect on the growth (see FIG. 6). One of them, named PTN4, containing like PTN1 two 4-chlorothiophenol motifs, was found active at a lover concentration (10 µM; FIG. 7 (A)). This analysis confirmed the activity of 4-chlorothiophenol structure. The importance of the sulfur environment was also highlighted as PTN5 and PTN6, which present additional bonds to methyl or oxygen, were found inactive (see FIG. 6 (C), (D)).

Detailed Analysis of PTN Impact on Root Growth

To better understand how PTN promoted root growth of −Pi seedlings, it was investigated the meristematic activity and the cell elongation rate, two key parameters of growth. Meristem activity was tested using the cell cycle marker cycB1::GUS. Cyclin B1 is expressed predominantly during G2/M phase of the cell cycle (Colón Carmona et al., 1999). As already described by (Sanchez-Calderon et al., 2005), this marker is expressed in the root meristematic zone of seedlings grown on +Pi medium, but not in −Pi seedlings. At 40 µM of PTN1, the CycB1 was expressed in the root tip of −Pi seedlings but there were fewer stained cells than in the +Pi control (see FIG. 7 (B)).

As published by Reymond et al. (2006), Pi starvation strongly reduces root cell elongation as monitored on epidermis cells. This observation was confirmed on cortical cells and it was found that their length is reduced by 50% (FIG. 7 (C)). Interestingly, PTN1 restored root cell elongation of −Pi seedlings to an extant closed to the untreated control grown on a +Pi medium (FIG. 7 (C)). These results showed that PTNs acted on both the meristematic activity and the cell elongation rate to sustain root growth on −Pi medium.

Since PTN somehow mimicked Pi, it was experimentally determined which external Pi concentration was necessary to obtain the same primary root growth as with 40 uM of PTN4 on a −Pi medium. In the range of Pi concentrations tested (15-250 uM), the primary root length was proportional to the external Pi (grey bars in FIG. 7 (D)). The addition of 10 uM of PTN4 (FIG. 7 (D)) or PTN1 (not shown) improved root growth until 50/75 µM of Pi. At 75 µM of Pi and above, no significant differences were observed between plants grown with or without PTNs. Interestingly, at Pi concentrations between 15 and 75 µM, the sustained growth promoted by PTNs was found seemingly independent of external Pi.

A few mutants altering root growth in response to low Pi were available offering additional tools to investigate the PTNs effects. The lpi mutants (Sanchez-Calderon et al., 2006), lpr1 and lpr2 (Svistoonoff et al., 2007) have been identified previously on the basis of their reduced sensitivity to Pi starvation effects on root architecture. When grown on −Pi medium they display a longer primary root than the WT control. Excepted lpr2, no additive effect of PTN1 or PTN4 were found to affect the primary root growth of lpr1 or lpi mutants (see FIG. 8). By contrast, the lpr2 mutant exhibited a moderate root length phenotype compared to lpr1 and lpi, and it responded to PTNs leading to a 50% increase of the primary root length (Fig S4).

The pdr2 mutant shows an hypersensitive response to low Pi and exhibits a very short primary root when grown on low Pi (Ticconi et al., 2004). Epistasis analysis indicates that PDR2 (coding for a P-type 5 ATPase) and LPR1 acted in a same functional pathway controlling the root growth response to −Pi (Ticconi et al., 2009). Interestingly, PTN1 substantially reverted the root growth defect of pdr2 (FIG. 7 (E)).

The response of phr1 mutant was also investigated because PHR1 was described as a major regulator of the transcriptional response to a Pi starvation (Franco-Zorrilla et al., 2004). Compared to the WT, the phr1 seedlings have a shorter primary root in both a −Pi and a +Pi medium (Bustos et al., 2010). Like for pdr2, phr1 responded to PTN1 which partially alleviated the of root growth restriction imposed by −Pi (FIG. 7 (E)).

These results showed that the LPR2, PDR2 and PHR1 functions are not essential for PTN1 to restore root growth in low Pi.

The primary root growth response to a Pi starvation has been shown to depend on the iron concentration in the medium (Svistoonoff et al., 2007; Ward et al., 2008). Indeed, reducing iron concentration in the medium suppressed root architecture modifications associated to Pi starvation. A hypothesis that could explain the PTN1 effect on root growth is the chelation of iron in a biologically inactive form. However, the absorption spectrum of a solution containing PTN1 and $Fe^{2+}$ ($FeCl_2$) is identical to the PTN1 control without $FeCl_2$ (see FIG. 9), suggesting an absence of chemical interaction between these two compounds.

This was reinforced by ICP analysis of the Fe content in plants (FIG. 9 (B)). The Pi starvation strongly increased the Fe content both in leaves and in roots as previously described (Hirsch et al., 2006). Nevertheless, PTN1 did not reduce the Fe content (FIG. 9 (B)). Accordingly to these chemical results, PTN1 action seemed to be independent of iron.

PTNs Reduced the Growth Restriction

As PTNs sustained root growth, it was investigated whether it also affects the development of the aerial part. Although plants cultivated four weeks on −Pi+PTN1 are not as big as those growing on +Pi, the PTN compound significantly improved leaf growth (+50% rosette area) on the −Pi medium (see FIG. 10 (A), (B)). Same results were obtained with PTN4 (data not shown). Together with results on roots, this showed that the PTNs substantially improve the whole plant growth in low Pi conditions, suggesting that these compounds unlock a mechanism restricting growth.

The accumulation of anthocyanin and starch in leaves are two others Pi-starvation responses shared by many plants (Poirier and Bucher, 2002; Ciereszko et al., 2001). As shown in FIGS. 10 (A), (C), and (D), PTN1 strongly reduced these two symptoms. Anthocyanin accumulated in PTN1-treated plants is around 60% less than in the control grown on −Pi (FIG. 10 (C)). Starch accumulation, as assessed by lugol staining, was also severely attenuated by PTN1 (FIG. 10 (D)). These results indicate that PTN1 reduced some main metabolic consequences associated with Pi starvation.

PTNs somehow phenocopy the growth and development of the lpr1 mutants. Indeed, the lpr1 plants display a long root (Reymond et al., 2006; Svistoonoff et al., 2007) and a larger rosette when grown in −Pi (see below). If LPR1 is the target of PTN (i.e. inhibits its expression our activity), then it was expected that the PTN did not improve further the growth of lpr1. When grown on −Pi conditions, lpr1 plants displayed a rosette 30% larger than in the WT control (FIGS. 10 (B) and 11). Unlike roots, PTN1 and PTN4 further increased the growth of the lpr1 rosette (+25%) (FIGS. 10 (D) and 11). It was also observed that leaves of lpr1 grown in −Pi were darker than in +Pi, most probably because of anthocyanins accumulation, and that PTN1 substantially suppressed this accumulation (FIG. 11). Therefore, although root growth of lpr1 is not improved by PTN, the aerial part still responded to PTNs.

The molecular responses of lpr1 when treated with PTN1 was also investigated. First, it was observed that the level of the induction of genes involved in Pi uptake (PHT1;4, PHT1;8), Pi recycling (MGD3, PLDz2, SQD2), and Pi signaling (SPX1) were similar between Col-0 and the mutant, grown in −Pi conditions (see FIG. 12). Second, PTN1 repressed the expression of these genes in lpr1 to a similar level as observed in the WT (FIG. 12).

Altogether, the growth and molecular results showed that the plant responses to PTN1 were not altered in the lpr1 mutant, suggesting that LPR1 is not a target of PTNs. However, it cannot be excluded the hypothesis that LPR1 is involved for root growth phenotype in presence of PTN1.

REFERENCES

Abel S (2011) Curr Opin Plant Biol. 14: 303-309
Arnaud C, et al. (2010) C R Biol. 333: 335-343
Bustos R, et al. (2010) PLoS Genet. 6
Ciereszko I, et al. (2001) Planta 212: 598-605
Colón Carmona A, et al. (1999) Plant J. 20: 503-508 del Pozo J C, et al. (1999) Plant J. 19: 579-589
Dormann P and Benning C (2002) Trends Plant Sci. 7: 112-118
Drew M C (1975) New Phytol. 75: 479-490
Franco-Zorrilla J M, et al. (2004) J Exp Bot. 55: 285-293
Gilbert N (2009) Nature 461: 716-8
Hirsch J, et al. (2006) Biochimie 88: 1767-1771
Hurley B A et al. (2010) Plant Physiol. 153: 1112-1122
Karthikeyan A S, et al. (2002) Plant Physiol. 130: 221-233
Kobayashi K et al., (2009) Plant J. 57: 322-331
Kolari K K and Sarjala T (1995) Tree Physiology 15: 747
Linkohr B I, et al. (2002) Plant J. 29: 751-760
Lopez-Bucio J, et al. (2002) Plant Physiol. 129: 244-256
Misson J, et al. (2004) Plant Mol Biol. 55: 727-741
Misson J, et al. (2005) Proc Natl Acad Sci USA 102: 11934-11939
Moellering E R and Benning C (2010) Trends in Plant Science
Mudge S R, et al. (2002) Plant J. 31: 341-353
Nagarajan V K, et al. (2011) Plant Physiol. 156: 1149-1163
Nakamura Y, et al. (2009) Proc Natl Acad Sci. 106: 20978
Narang R A, et al. (2000) Plant Physiol. 124: 1786-1799
Nussaume L, et al. (2011) The Plant Plasma Membrane: 237-251
Peret B, et al. (2011) Trends Plant Sci. 16: 442-450
Poirier Y and Bucher M (2002) The *Arabidopsis* Book
Raghothama K G (1999) Annu Rev Plant Physiol Plant Mol Biol. 50: 665-693
Reymond M, et al. (2006) Plant Cell Environ. 29: 115-125
Rouached H, et al. (2011) Plant J. 65: 557-570
Rubio V, et al. (2001) Genes Dev. 15: 2122-2133
Sanchez-Calderon L, et al. (2005) Plant Cell Physiol. 46: 174-184
Sanchez-Calderon L, et al. (2006) Plant Physiol. 140: 879-889
Shen J, et al. (2011) Plant Physiol. 156: 997-1005
Shin H, et al. (2004) Plant J. 39: 629-642
Svistoonoff S, et al. (2007) Nat Genet. 39: 792-796
Thibaud M C, et al. (2010) Plant J. 64: 775-789
Ticconi C A, et al. (2001) Plant Physiol. 127: 963-72
Ticconi C A and Abel S (2004) Trends in Plant Science 9: 548-555
Ticconi C A, et al. (2004) Plant J. 37: 801-814
Ticconi C A, et al. (2009) Proc Natl Acad Sci USA 106: 14174-14179
Tran H T, et al. (2010) Plant Science 179: 14-27
Ward J T, et al. (2008) Plant Physiol. 147: 1181-1191
Zakhleniuk O V, et al. (2001) Planta 212: 529-534
Zhao Y, et al. (2007) Nature Chemical Biology 3: 716-721

The invention claimed is:

1. A method for promoting growth of a plant, comprising adding to growing medium or soil in which the plant is grown a compound of formula (I):

$$A\text{-}R_1 \quad (I)$$

wherein

A represents a 4-chlorothiophenol group of formula (II):

(II)
Cl—⟨phenyl⟩—S— linked to $R_1$ through its sulfur atom, $R_1$ represents:
- a hydrogen atom;
- a group A as defined above, linked to the first group A through its sulfur atom;
- an electroattractive group selected from the group consisting of
  O—R, S—R, CO—R and Ar—R, wherein R represents an unsubstituted or substituted, linear or branched $C_1$-$C_6$ alkyl group, a $C_1$-$C_6$ alkoxy group, a $C_1$-$C_6$, alkenyl group, a $C_1$-$C_6$ alkynyl group and an aromatic $C_4$-$C_6$ group, optionally substituted by a group selected from the group consisting of oxygen, sulfur, a halogen atom, NH, $NH_2$, OH, and an unsubstituted or substituted $C_1$-$C_6$ alkyl group, where Ar represents a $C_4$-$C_6$ aromatic group
- Ar-A, wherein Ar and A are as defined above
- $R_2$-A, wherein:
  $R_2$ represents an unsaturated $C_4$-$C_6$ cycle, optionally substituted with at least one oxygen atom, where the oxygen atom is linked by a double bond to the $C_4$-$C_8$ cycle;
  A is a group as defined above, linked to $R_2$ through its sulfur atom; and
- a group of formula (III):

(III)

$$\overset{O}{\underset{\|}{-C}}-B-\overset{R_3}{\underset{R_5}{\overset{|}{S}}}-R_4,$$

wherein
B represents an unsaturated $C_5$-$C_6$ monocycle or a fused bicycle in which each cycle is an unsaturated $C_5$-$C_6$ cycle, optionally substituted with a linear or branched $C_1$-$C_6$ alkyl group;

$R_3$ and $R_5$ are identical or different, and represent independently a group selected from the group consisting of oxygen, sulfur, a halogen atom, NH, $NH_2$, OH, and an unsubstituted or substituted $C_1$-$C_6$ alkyl group;

$R_4$ represents a linear or branched unsubstituted or substituted $C_1$-$C_6$ alkyl group.

2. The method according to claim 1, wherein the plant which is growing in the growing medium or soil in which the compound of formula (I) is being added to is *Arabidopsis thaliana*.

3. The method according to claim 1 wherein the compound of formula (I) is selected from the group consisting of PTN1 of formula (IV):

(IV)

PTN2 of formula (V)

(V)

PTN3 of formula (VI)

(VI)
HS—⟨phenyl⟩—Cl and

PTN4 of formula (VII)

(VII)

4. The method according to claim 1, wherein the plant is grown under phosphate limiting conditions.

* * * * *

SEQUENCE LISTING

```
<160> NUMBER OF SEQ ID NOS: 24

<210> SEQ ID NO 1
<211> LENGTH: 2998
<212> TYPE: DNA
<213> ORGANISM: Arabidopsis thaliana

<400> SEQUENCE: 1
tccttgttca taggcagctt caacgatcat tccacttcct tcttcctctc tctcaacatt      60
ttcccctgaa aataaggaaa ctaaagattc ttcctctctc tttctacact cttctgacaa     120
```

```
tactaaaaca ctttatcaga tcagatccca cataaacttt ctgtaagtgt ttcttttaaa    180
ctatgtctgt tgatgttaat gtttatggat gcataatgat tttagttagg acgttatcgt    240
ttttgttttg ttaggtggtc ctctctccct gttcaatctc taattcgtca tgtcttattc    300
gtttctttca ttggaaaaaa aacactgaaa actagttttt gttttttccaa ctttcttgga    360 tcattaaata ggattgctct ctcttcaaac gtattttgt tggatctctc ctcttcagtt     420
ctagaagact ttttttttt tccttttgtt gagtgcatga tttcaaaaaa tttcaattga     480
agaagtttgt gatatttgt tgttttctt cttcaataag aggtgtgtcc gcaattaaga     540
caaaacaact cgctgtcata ctcagttaaa gtctttgttg ctcgtgttca gattttcact    600
agacgtcaca agtcaacttt tgtgggtaac tgaagacaaa tagtaatcgt tgaaaactac    660
aataataaaa taagtacttc cagtgtctcc gttcacctt aaaaagtcga gataaaccca    720
aaaaaatagg aataaacaat cttttgtcat atccgttaat aagttttaac aaatctttac    780
aaattaataa gaagaacgta tataataaat atttcaaaat taacgagtgt ggactaatat    840
tgagttgact tttattatca cttcatttca gttccttgaa tatgcatata ctgtatatgg    900
tttctcttgc ataagtaag catcatacat atgtacagga acatgagaag ttgtcgttaa    960
caactacttc atctaaaaaa catacacatg ttatttttct aatattgcct gacttcaagt   1020
tcggtgaaca tactttattg ggttgtaatt gtgagatcaa tgaaatgaga aaattaaat   1080 agaacttta tgatatttta atgttaattg atactatata aagcagggtc taattctatt   1140
tgcttttaaa actgcctaac ttatttcaag ttcggtataa ctaactactt tattgtttgt   1200
aatgagttat ttaagggtac ttatatgtcg aactttttt tgtgtgatga aaaattgcag    1260
aggagaagaa gaatgcaag ggaacaatta caagtgttga atgcacttga cgtggccaag    1320
acgcaatggt accatttcac ggcgatcata atcgccggaa tgggattctt cactgatgct   1380
tacgatctct tttgcatctc tctcgtaacg aagctcctcg gtcgtatta ttaccacgtg    1440 gaaggcgcac aaaagcctgg gactctccct cccaacgtcg cagccgccgt caatggcgtt   1500
gccttctgtg ggactctcgc cggtcagctc tttttcgggt ggcttggtga taagctcggg   1560
aggaagaaag tttacggtat gacgttgatg gtcatggtcc tttgttcaat agcctctggt   1620
ctctctttcg gacatgagcc aaaagctgtg atggccacgc tctgttttt tcggttttgg   1680 cttggatttg gcatcggtgg tgactaccct ttatccgcaa ccatcatgtc tgaatatgcg   1740
aacaagaaga ctcgcggagc ctttgtctct gcggttttg ctatgcaagg gttcggaatc   1800
atggctggtg gtatttcgc tattataatt tcctctgctt ttgaagctaa gtttccatcc   1860
ccggcctatg cggatgatgc cttgggatcc acgattcctc aagctgattt ggtatggcgg   1920
ataatcctga tggctggtgc tatccctgcg gctatgacgt attactcaag gtcgaagatg   1980
cctgagaccg caaggtacac ggctttggtt gctaaggacg caaagcaggc agcttcggac   2040
atgtctaagt ttctgcaagt ggagatagag ccagaacaac agaaattgga agagatctca   2100
aaggagaagt ccaaggcctt tggattgttc tcaaaggaat tcatgagtcg ccatgggctt   2160
catttgctag gcactacatc gacatggttc cttctcgaca ttgctttcta cagtcaaaac   2220
cttttccaaa aggatatttt cagcgcgatc ggatggattc ctcccgcgca aagcatgaac   2280
gcaattcaag aggttttcaa gattgcccgt gcgcaaacgc taatcgcctt gtgtagcacg   2340
gtacctggtt actggttcac agttgcgttc atcgacgtca ttggaagatt tgcgattcag   2400
atgatgggtt tctttttcat gacggtcttt atgtttgctc tggctattcc ttacaaccac   2460
```

```
tggactcaca aggagaaccg aatcggattt gttatcatgt actcgttaac attcttttc    2520 gccaactttg gacccaatgc tacaaccttc gttgtgccgg ccgaaatctt cccagccagg    2580
ttcagatcaa cctgccacgg tatctctgca gcatcaggaa aattaggagc aatggttggt    2640
gcgttcgggt tcttgtactt ggctcagaac ccagacaagg acaagaccga cgcaggatac    2700
cctccaggga ttggggtcag gaactcgctt attgtgttgg gtgtagttaa cttcttaggt    2760
atcctcttca ctttcttggt acctgaatct aaaggtaagt cactcgagga aatgtccggt    2820
gaaaatgaag acaatgagaa tagcaacaat gatagtagaa cggtcccaat agtttaggtg    2880
atataatacg cctttgtaa taattttcgt tttttctttc tccttgtctc tagcaactca    2940
agttgttctt tgtgtaatcc attgatacct aattaatgct agagaaatca aaattttc     2998
```

<210> SEQ ID NO 2
<211> LENGTH: 534
<212> TYPE: PRT
<213> ORGANISM: Arabidopsis thaliana

<400> SEQUENCE: 2

```
Met Ala Arg Glu Gln Leu Gln Val Leu Asn Ala Leu Asp Val Ala Lys
1               5                   10                  15

Thr Gln Trp Tyr His Phe Thr Ala Ile Ile Ala Gly Met Gly Phe
            20                  25                  30

Phe Thr Asp Ala Tyr Asp Leu Phe Cys Ile Ser Leu Val Thr Lys Leu
        35                  40                  45

Leu Gly Arg Ile Tyr Tyr His Val Glu Gly Ala Gln Lys Pro Gly Thr
    50                  55                  60

Leu Pro Pro Asn Val Ala Ala Val Asn Gly Val Ala Phe Cys Gly
65                  70                  75                  80

Thr Leu Ala Gly Gln Leu Phe Phe Gly Trp Leu Gly Asp Lys Leu Gly
            85                  90                  95

Arg Lys Lys Val Tyr Gly Met Thr Leu Met Val Met Val Leu Cys Ser
        100                 105                 110

Ile Ala Ser Gly Leu Ser Phe Gly His Glu Pro Lys Ala Val Met Ala
    115                 120                 125

Thr Leu Cys Phe Phe Arg Phe Trp Leu Gly Phe Gly Ile Gly Gly Asp
130                 135                 140

Tyr Pro Leu Ser Ala Thr Ile Met Ser Glu Tyr Ala Asn Lys Lys Thr
145                 150                 155                 160

Arg Gly Ala Phe Val Ser Ala Val Phe Ala Met Gln Gly Phe Gly Ile
            165                 170                 175

Met Ala Gly Gly Ile Phe Ala Ile Ile Ile Ser Ser Ala Phe Glu Ala
        180                 185                 190

Lys Phe Pro Ser Pro Ala Tyr Ala Asp Asp Ala Leu Gly Ser Thr Ile
    195                 200                 205

Pro Gln Ala Asp Leu Val Trp Arg Ile Ile Leu Met Ala Gly Ala Ile
210                 215                 220

Pro Ala Ala Met Thr Tyr Tyr Ser Arg Ser Lys Met Pro Glu Thr Ala
225                 230                 235                 240

Arg Tyr Thr Ala Leu Val Ala Lys Asp Ala Lys Gln Ala Ala Ser Asp
            245                 250                 255

Met Ser Lys Val Leu Gln Val Glu Ile Glu Pro Glu Gln Gln Lys Leu
        260                 265                 270

Glu Glu Ile Ser Lys Glu Lys Ser Lys Ala Phe Gly Leu Phe Ser Lys
    275                 280                 285
```

-continued

Glu Phe Met Ser Arg His Gly Leu His Leu Leu Gly Thr Thr Ser Thr
    290                 295                 300

Trp Phe Leu Leu Asp Ile Ala Phe Tyr Ser Gln Asn Leu Phe Gln Lys
305                 310                 315                 320

Asp Ile Phe Ser Ala Ile Gly Trp Ile Pro Pro Ala Gln Ser Met Asn
                325                 330                 335

Ala Ile Gln Glu Val Phe Lys Ile Ala Arg Ala Gln Thr Leu Ile Ala
            340                 345                 350

Leu Cys Ser Thr Val Pro Gly Tyr Trp Phe Thr Val Ala Phe Ile Asp
        355                 360                 365

Val Ile Gly Arg Phe Ala Ile Gln Met Met Gly Phe Phe Phe Met Thr
    370                 375                 380

Val Phe Met Phe Ala Leu Ala Ile Pro Tyr Asn His Trp Thr His Lys
385                 390                 395                 400

Glu Asn Arg Ile Gly Phe Val Ile Met Tyr Ser Leu Thr Phe Phe Phe
                405                 410                 415

Ala Asn Phe Gly Pro Asn Ala Thr Thr Phe Val Val Pro Ala Glu Ile
            420                 425                 430

Phe Pro Ala Arg Phe Arg Ser Thr Cys His Gly Ile Ser Ala Ala Ser
        435                 440                 445

Gly Lys Leu Gly Ala Met Val Gly Ala Phe Gly Phe Leu Tyr Leu Ala
    450                 455                 460

Gln Asn Pro Asp Lys Asp Lys Thr Asp Ala Gly Tyr Pro Pro Gly Ile
465                 470                 475                 480

Gly Val Arg Asn Ser Leu Ile Val Leu Gly Val Val Asn Phe Leu Gly
                485                 490                 495

Ile Leu Phe Thr Phe Leu Val Pro Glu Ser Lys Gly Lys Ser Leu Glu
            500                 505                 510

Glu Met Ser Gly Glu Asn Glu Asp Asn Glu Asn Ser Asn Asn Asp Ser
        515                 520                 525

Arg Thr Val Pro Ile Val
    530

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
caacttgagg aggcgttga                                                19

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ggttttggtt gggatttgg                                                19

<210> SEQ ID NO 5
<211> LENGTH: 23
<212> TYPE: DNA
<213> ORGANISM: Artificial Sequence
<220> FEATURE:

```
<223> OTHER INFORMATION: Primer

<400> SEQUENCE: 5
gactacccac tttctgccac cat                                              23

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ctttcctcaa gctcgatatc tgt                                              23

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cctcggtcgt atttattacc acg                                              23

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ccatcacagc ttttggctca tg                                               22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
cgttgttgat gcttgcttgt                                                  20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ctaccggaat ttgccacagt                                                  20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tccctcattg ttttgggtgt                                                  20
```

```
<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gttcgttctc accggacatt                                              20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aaacgccacc aagaatcaag                                              20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tcccggctag gtttaggtct                                              20

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
acaagaaatt ggcatctgca t                                            21

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tggtccagct tttgtgatga                                              20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
agaggccggt ttaatggagt                                              20

<210> SEQ ID NO 18
<211> LENGTH: 20
<212> TYPE: DNA
<213> ORGANISM: Artificial Sequence
<220> FEATURE:
<223> OTHER INFORMATION: Primer
```

```
<400> SEQUENCE: 18
catcagagga tgcacgctaa                                              20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tacctgaagc tcggattgct                                              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tgtgagagtt catcgccttg                                              20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
agcttgggct agacgtgaaa                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
aggctcaagt ccaagttcca                                              20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tgcattgctg gagacaaaag                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ttttgaagcc gtttcttgct                                              20
```